(12) United States Patent
Zaleski

(10) Patent No.: US 11,497,456 B2
(45) Date of Patent: Nov. 15, 2022

(54) ALARM SETTING DERIVED FROM THE VARIABILITY IN SIGNAL CHARACTERISTICS

(71) Applicant: PHILIPS CAPSULE CORPORATION, Cambridge, MA (US)

(72) Inventor: John Zaleski, Elkton, MD (US)

(73) Assignee: PHILIPS CAPSULE CORPORATION, Cambridge, MA (US)

(*) Notice: Subject to any disclaimer, the term of this patent is extended or adjusted under 35 U.S.C. 154(b) by 163 days.

(21) Appl. No.: 16/360,376

(22) Filed: Mar. 21, 2019

(65) Prior Publication Data

US 2020/0077965 A1  Mar. 12, 2020

Related U.S. Application Data

(60) Provisional application No. 62/646,052, filed on Mar. 21, 2018.

(51) Int. Cl.
*A61B 5/00* (2006.01)
*G06F 17/18* (2006.01)

(52) U.S. Cl.
CPC ........... *A61B 5/746* (2013.01); *A61B 5/0002* (2013.01); *A61B 5/7282* (2013.01); *G06F 17/18* (2013.01)

(58) Field of Classification Search
CPC ..... A61B 5/746; A61B 5/0002; A61B 5/7282; A61B 5/7246; A61B 5/02455; A61B 5/02405; G06F 17/18
See application file for complete search history.

(56) References Cited

U.S. PATENT DOCUMENTS

| | | | |
|---|---|---|---|
| 9,131,883 B2* | 9/2015 | Al-Ali | A61B 5/0402 |
| 10,685,549 B2* | 6/2020 | Zaleski | A61B 5/746 |
| 2006/0167365 A1* | 7/2006 | Bharmi | A61B 5/364 600/517 |
| 2014/0066884 A1* | 3/2014 | Keenan | G16H 20/17 604/504 |
| 2015/0272515 A1* | 10/2015 | Paquet | G16H 40/67 600/300 |
| 2016/0155309 A1* | 6/2016 | Watson | A61B 5/7282 600/324 |
| 2016/0321904 A1* | 11/2016 | Johnson | G16H 40/20 |
| 2017/0095634 A1* | 4/2017 | Miller | A61M 16/12 |
| 2018/0055373 A1* | 3/2018 | Kraiter | A61B 5/1118 |
| 2018/0078219 A1* | 3/2018 | Selvaraj | A61B 5/746 |
| 2018/0338731 A1* | 11/2018 | Addison | G16H 50/20 |

* cited by examiner

*Primary Examiner* — Catherine M Voorhees

(57) ABSTRACT

A method for creating alarm signals based on time-series signal behavior determined from real-time discrete data obtained from a medical device. In one embodiment the method includes identifying patterns in preceding time-series measurement threshold breaches in clinical readings obtained from said medical device when associated with a particular patient, and initiating an alarm signal to a front-line clinician based on the preceding quantity of threshold breaches.

8 Claims, 22 Drawing Sheets

ALARM SETTING DERIVED FROM THE VARIABILITY IN SIGNAL CHARACTERISTICS

CROSS REFERENCE TO RELATED APPLICATIONS

This application claims priority to and benefit of U.S. Provisional Application No. 62/464,052 filed on Mar. 21, 2018, the entire disclosure of which is incorporated by reference herein.

FIELD OF TECHNOLOGY

The invention relates generally to a method for creating alarm signals based on time-series real-time discrete data obtained from a medical device and more specifically, to identifying patterns in preceding time-series measurement threshold breaches in clinical readings obtained from the medical device.

BACKGROUND

Many documentation systems in acute care settings of healthcare enterprises employ a user interface for documenting clinical information such as patient vital signs, infusions, outputs such as blood and urine flow, laboratory values, notes, images, and orders. Some of these documentation systems include the recording of alarm system events intended for real-time intervention when patients are experiencing emergencies. These emergencies often require immediate response as a matter of survival.

Historically, medical devices such as physiologic monitors, mechanical ventilators, etc., record live physiologic signals, such as cardiorespiratory measurements including, but not limited to, heart rate, breathing rate, and blood pressure. These devices then provide the data to documentation systems for continuous management of a patient's status.

These medical devices produce alarm signals in addition to the measurement data, and the alarm signals are intended to provide general notice, warning, and crisis-level notice to the clinicians when certain events are deemed to be of an emergent or potentially life threatening nature. For example, identification of asystole, ventricular tachycardia or fibrillation, high peak pressure, low tidal volume, and cessation of breathing are events that would merit emergency intervention.

Machine-generated alarm signals are often communicated to central monitoring stations separate from the signals provided to clinical documentation systems as these monitoring stations provide for the review of real-time data intended for interventional guidance to the clinician. These central monitoring stations are intended to provide live and real-time oversight of patient physiological measurements for the express purpose of identifying current status of the patient's vital signs, especially the cardiorespiratory parameters.

Alarm signals issued by the medical devices are typically reactive in nature—meaning they are issued when an identified event occurs. Examples of such events are a threshold limit breach in a particular physiological measurement as listed as examples above. These alarm signals are often transmitted to alarm communication systems for remote notification of clinical staff when the clinicians are not immediately present at the point of care. The communication and display of alarm signals generated by medical devices are functions which will be referred to as being provided by an alarm system.

Historically, alarm systems are static in that they: (1) do not permit dynamic manipulation of alarm thresholds in real-time; (2) are limited in that they require alarm thresholds to be set by clinicians; (3) are not capable of being changed remotely; (4) do not have analytical tools to determine alarm thresholds in real time; (5) do not provide an easy and simple way to toggle between alarm thresholds; (6) do not provide the capability to alter or manipulate alarm thresholds based on the frequency of alarms; (7) do not provide the capability to create new types of alarm signals based on the characteristics of the data based on observed signal behavior, nor tailor these new types of alarm signals based on characteristics of the patient; and (8) do not enable the incorporation of external or secondary information that could inform the user as to whether an alarm is actionable clinically or not. Examples of external or secondary information could include indications of the existence of signal artefacts that could invalidate measurements obtained from a sensor, such as calibration issues or sensor disconnects. This lack of flexibility frequently results is alarms being issued that are unnecessary, causing interruption of the care of other patients.

The lack of flexibility can translate into a lack of skill in terms of the accuracy with which reactive medical device alarm signals can detect and discriminate between clinically-actionable indications in the patient and artefact-based signals that carry no clinical importance. This latter event is oftentimes referred to as the occurrence of false alarms.

What is needed is a method to reduce the number of false alarms. The present invention provides an approach for addressing this need.

SUMMARY

In one aspect, the present application is directed to a method for creating a notification based on time-series signal behavior from a medical device monitoring a patient. In one embodiment the method includes the steps of identifying preceding threshold breaches in a patient's clinical readings within a specified time-frame. The threshold breaches are defined with respect to a control limit as a deviation from common baselines. The time-series measurement signal is a running average of the signal over a specified duration. An alarm signal is issued based upon a deviation meeting specific criteria, such as detecting a pre-specified quantity of threshold breaches within a pre-defined duration over an agreed-to running average period. These signal notifications are, essentially, new alarm signals which are generated with the intention of communicating patient issues to clinical staff. The aggregation of the signal measurements in the manner described above effectively reduces the overall quantity of single measurement threshold breaches to a single notification based upon aggregated signal behavior according to the method described above.

In another embodiment, the step of identifying preceding threshold breaches in a patient's clinical readings includes the steps of continuously monitoring the patient and adjusting the thresholds based on the quantity of such breaches that have occurred previously. In this way, the notification to clinical staff can be based on the frequency with which historical threshold breaches occur. The quantity of notifications generated is based upon the number of acceptable threshold breaches above a pre-determined threshold, and may be customized based on the measurements obtained from a specific patient. The benefit of this customization or personalization of alarm signal thresholds based upon specific patient patterns, is that alarm signal notifications are tailored to the patient and, are more sensitive to specific patient signal measurement patterns.

The generation of notifications uses a method of calculating a running average over a defined time interval; setting the upper and lower thresholds in response to the running average; determining a breach of the upper or lower thresholds; and calculating changes in the thresholds if the number of breaches of the upper and lower thresholds exceeds a predetermined amount. This method is similar to methodologies used for signal frequency analysis, such as Periodograms or Fourier transforms, but is based purely on the time-series signal behavior without involving transformations of the signal to frequency space.

The notifications issued based on the calculations above are henceforward referred to as instability alerts as they pertain to deviations in the signal from a stable running average.

BRIEF DESCRIPTION OF DRAWINGS

Various features of the embodiments described herein, together with advantages thereof, may be understood in accordance with the following description taken in conjunction with the accompanying drawings as follows:

FIG. 14 illustrates the integration of the instances of individual breaches depicted in FIG. 13.

FIG. 15 is the equivalent of a moving average over a specific epoch of time, where the independent variable is the integral of individual threshold breaches, $I_{t_q}$, depicted in FIG. 14, and the time epoch is the window in time over which the integration is performed. An equivalent way of stating this in vernacular is FIG. 15 shows the average integral of threshold breaches over a defined time epoch.

FIG. 23 is a flowchart of an embodiment of a method of adjusting the for instability alert computation for a signal measurement.

DETAILED DESCRIPTION

Figure 1:
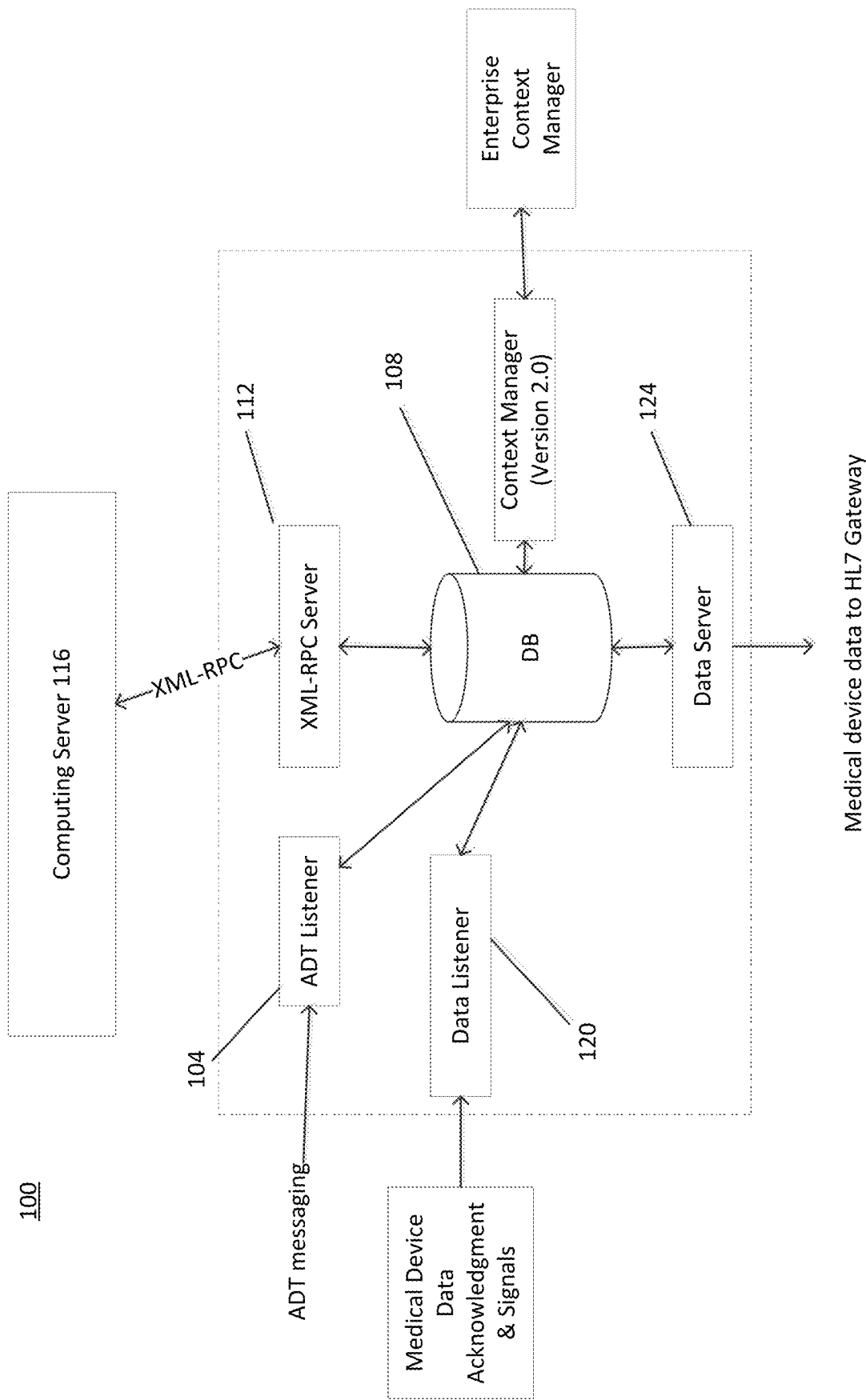
FIG. 1 is a block diagram of an embodiment of a system implementing the method of adjusting signal measurement thresholds associated with the issuing of instability alert notifications.

FIG. 1 is a block diagram of an alarm system for implementing the described method. In one embodiment the system 100 includes an ADT Listener 104 configured to receive patient demographic traffic and populate a database 108, and an XML-RPC Server 112 (as determined by a particular embodiment of the system architecture) configured to communicate data to a user-interface on a server or other computer 116 and generate notifications sent to a user based on the threshold(s) and/or user defined rules. The system also includes a data listener 120 configured to communicate with a system for medical device traffic, and a data server 124 configured to communicate validated data measurements to outbound Health Level Seven (HL7) Interface Engine. One embodiment involves communicating HL7 data through the Bernoulli One System (Bernoulli Enterprise, Inc., Milford, Conn. 06460) to electronic health record systems.

In some embodiments, XML-RPC Server 112 includes a notification tool configured to send a notification to the user when a parameter satisfies a user-defined rule and/or exceeds a threshold value. In various embodiments, computing device 116 can be used any computing device, e.g., a smartphone, tablet PC, laptop computers, etc., configured to display user-interfaces described herein. It should be understood by those of ordinary skill in the art that XML-RPC server 112 and computing device 116 are only examples and that other types of servers and computing devices are further contemplated according to aspects of the present invention. In various embodiments, multiple types of physiologic monitors systems communicate through an HL7 gateway, and traffic is differentiated by patient specific identifiers and location.

A review of the telemetry data from a sampling of patients, shows that a trend in increasing signal variability appears to correlate with the telemetry-monitor-issued crisis alarms. The present invention makes use of this increasing variability to herald the onset of telemetry-monitor-issued crisis alarms.

A number of existing methodologies using signal processing exist for evaluating the variability of signals emanating from the patient monitors. These methodologies include Fourier Transforms, Periodograms, etc. These methodologies are successful to varying degrees but an objective of the invention is to create a metric that is relatively simple and employs techniques that were not far-afield within the existing monitoring platforms, such as the Bernoulli One platform.

To this end, the present invention uses a combination of signal deviation and quantities of such deviations over some defined time interval to generate a signal variability measure. This signal variability measure is termed an "Instability Surveillance Calculation", or ISC, in order to differentiate it from signal variability—such as heart rate variability—which is uniquely defined and understood in the field. Furthermore, the metric ISC can be applied to any signal, not just those associated with heart rate measurement. The Instability Surveillance Calculation outputs an Instability Alert signal or message that is subsequently transmitted to frontline clinical personnel for action.

In one embodiment, the present invention describes the application of the Instability Alert to detecting heart rate instability, indicating the imminent onset of crisis or warning monitoring alarms issued by a physiologic monitoring system. This embodiment of the Instability Alert, termed heart rate instability, or HRI, alarm derives from variability in signal characteristics determined from the discrete data measurement of heart rate through physiologic monitoring data sampling. In one embodiment such patient monitoring is performed by a General Electric Telemetry Monitor (GE Healthcare, Wauwatosa, Wis., USA, 53226) The discrete data measurement is important as this type of alarm does not derive from the continuously-monitored waveform signal data (i.e., electrocardiogram waveform) but, rather, from the discrete heart rate measurement issued by the physiologic monitor.

Discrete measurements can be taken and issued at various rates. For the purpose of this alarm, the discrete heart rate measurements are issued at the rate of not less than one measurement every two seconds or thirty beats per minute. The discrete data form the basis for four specific characterizations of the discrete signal data from which an alarm annunciation is created.

Figure 2:
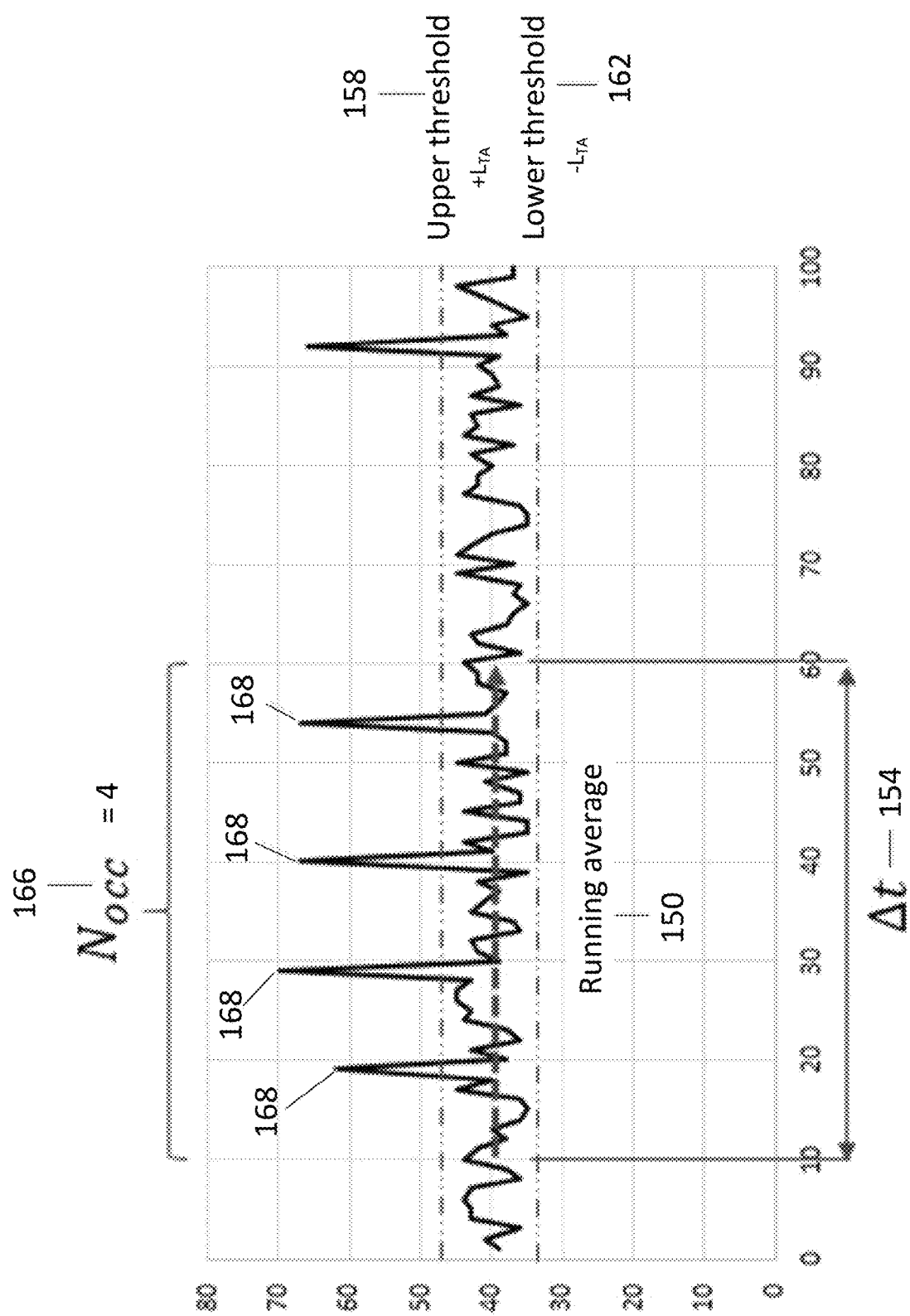
FIG. 2 is a diagram of an embodiment of a waveform showing the components by which the instability alert is calculated.

FIG. 2 is an example of a heart rate waveform used in the generation of a Heart Rate Instability (HRI) alarm. A running average 150 is calculated to establish a signal baseline over a user defined time interval 154 denoted ($\Delta t$). The time interval is normally based on the usual units of the signal (e.g. seconds, minute or hours). The upper and lower limit thresholds 158, 162 respectively are then defined with respect to the running average (the running average $\pm L_{TA}$). The number 166 of threshold breach occurrences 168 over the time interval 154 is defined as $N_{OCC}$. The number $L_A$ is the number $N_{OCC}$ of threshold breach occurrences 168 that must occur within a given time interval 154 prior to taking an action, such as the generation of a Heart Rate Instability Alarm. In other words, a running average is taken from t=0 to t+$\Delta t$, and at time (t+$\Delta t$) you determine if the signal value is outside the range of the running average (at time t+$\Delta t$) $\pm L_{TA}$.

In one embodiment, the upper and lower thresholds 158, 162 are defined as a percentage or fraction (e.g. 30% or 0.30) of the running average value. Value selection is based on past history and research, and may also be clinician-selected. For example, studies currently show that a value of 0.3 seems to be within a sufficient starting value. Parametric assessments using actual patient data have revealed that the sensitivity of the instability alert maximizes in terms of detecting the occurrence of the crisis alarm when this value is in the range of 0.3, and this sensitivity decreases markedly as 0.4 is reached. Conversely, selecting lower values than 0.3, results in hypersensitivity in terms of the production of the quantity of instability alerts. The number of times that a signal value exceeds or breaches the upper and lower limit thresholds 158, 162 within the interval 154 establishes the limit quantity $N_{OCC}$ that is compared with the clinician defined quantity threshold $L_A$.

For example, in a study of telemetry-based heart rate, analysis of the heart rate showed correlations of Heart Rate Instability (HRI) alarms prior to patient events requiring a rapid emergency response by the clinical staff. Retrospective analysis of the raw heart rate measurements showed that the occurrence of instability alerts tended to precede the onset of emergency or crisis alarms. Furthermore, the cumulative or integrated quantity of individual instability alerts tended to parallel the cumulative or integrated quantity of machine-issued crisis alarms. The instability alerts, computed independently of the machine-issued crisis alarms, when integrated over time, showed a high correlation to the integrated crisis alarms. The average correlation coefficient between integrated instability alerts and crisis alarms was computed to be 0.85 for all analyzed cases, N=29. This quantity was derived from a cohort of 20 patient locations in a telemetry unit over 30 days of continuous monitoring.

Figure 3:
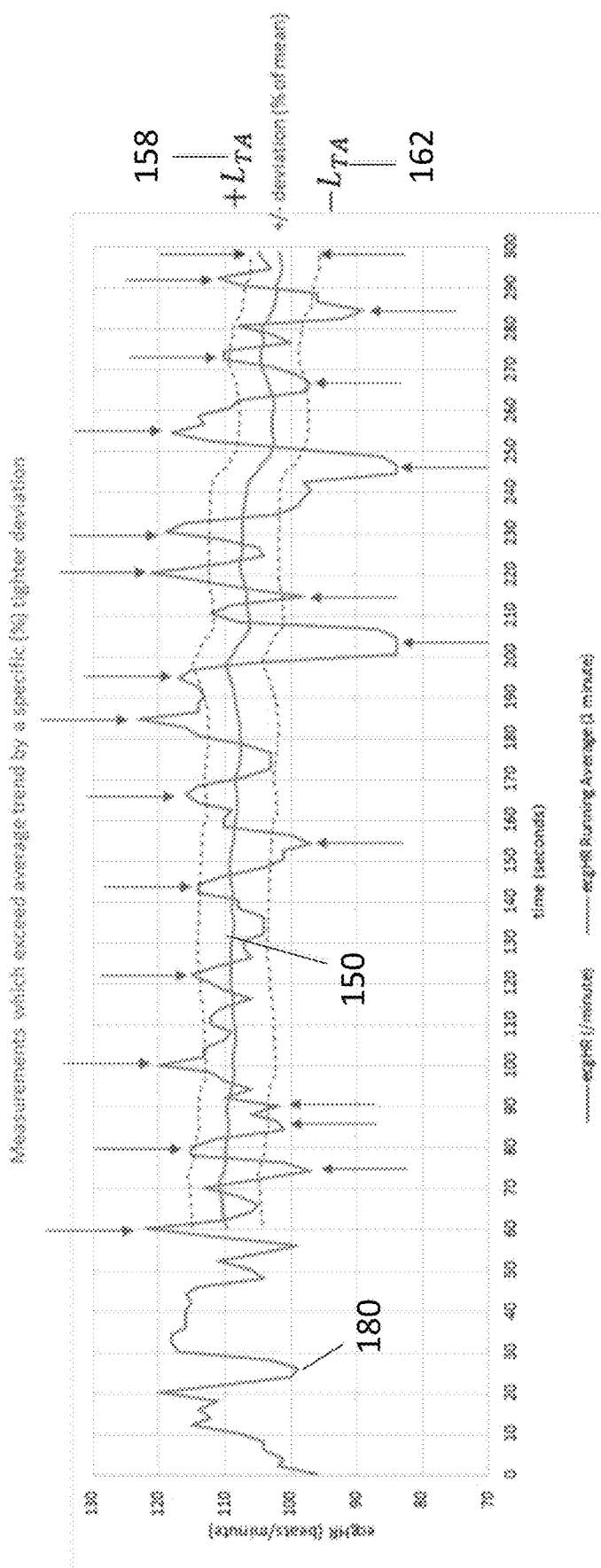
FIG. 3 is a graph of a heart rate measurement signal with multiple breach events that can cause the issuing of an instability alert.

FIG. 3 is a plot showing the measurements that meet the criterion for counting as a threshold breach by exceeding the average trend line by either a positive or negative amount, $\pm L_{TA}$. The instantaneous heart rate 180 is plotted along with the trend lines. The running average 150 is represented by the solid central line. The running average is calculated continuously based upon the receipt of new measurements from the medical device. The reason for computing the running average is to establish a localized baseline of patient signal measurements from which to evaluate and assess whether subsequent deviations of signal measurements are significant; with the term significant defined with respect to the deviation threshold, $\pm L_{TA}$. The duration of the running average interval in this example is a duration of 60 seconds. The rate of data arrival in this example is one measurement every 2 seconds. Thus, as each new measurement is obtained, the running average is re-computed by adding the additional measurement and removing the oldest measurement in the queue. Thus, the signal running average of 1-minute is computed and advanced along the timeline at the rate of signal measurement (i.e., 2 seconds) every time a signal measurement is obtained. The dashed lines represent a deviation from the running average line 150, defined by the limit thresholds $\pm L_{TA}$ 158, 162 which are a percentage of the mean signal as described above. When the limit thresholds are a smaller percentage of the running average, the likelihood that any individual measurement will deviate from the running average is higher, especially if the signal is a noisy signal. The arrows in the figure indicate where the local maximum value of the signal measurements exceeds threshold limits.

Figure 4:
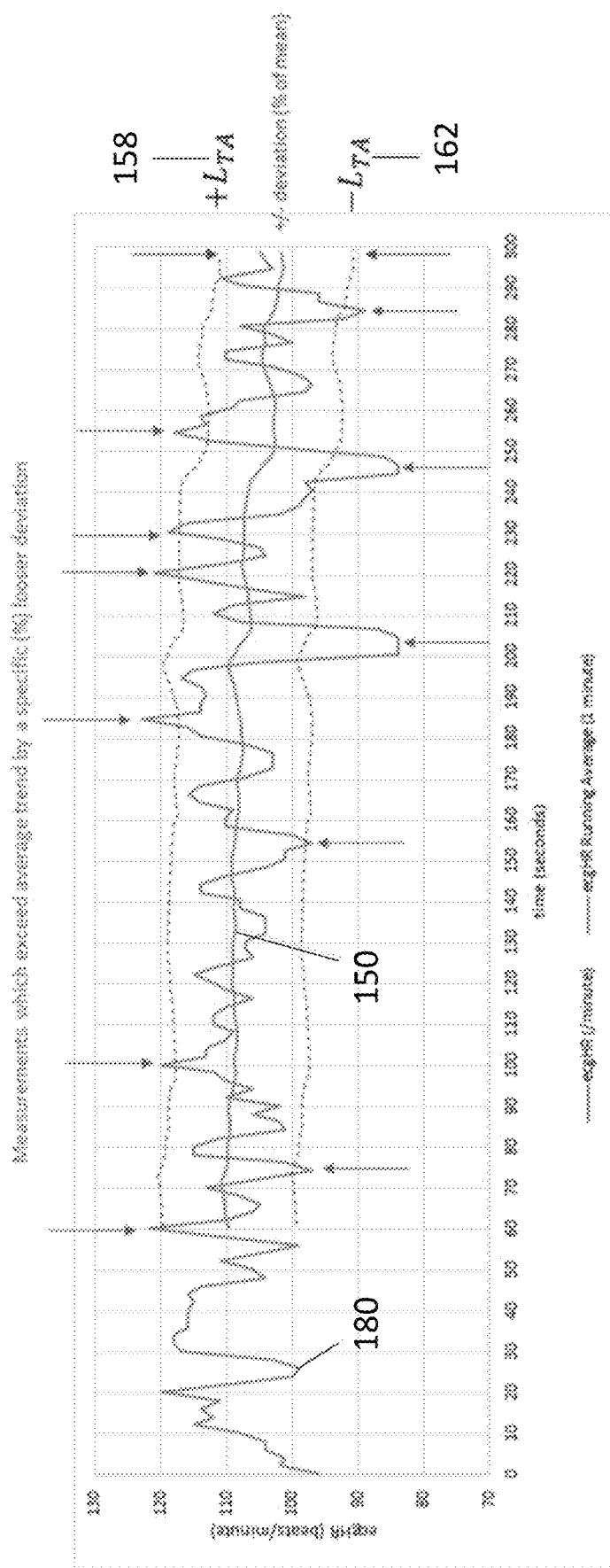
FIG. 4 is a graph of the heart rate measurement signal of FIG. 3 depicting the effect of changes in the limit threshold on the number of breach events.

FIG. 4 illustrates what happens when the limit thresholds are relaxed or set larger: a general reduction in episodes in which individual measurements are found to deviate from the running average 150. As the limit thresholds are increased, the likelihood of threshold breaches decrease.

Figure 5:
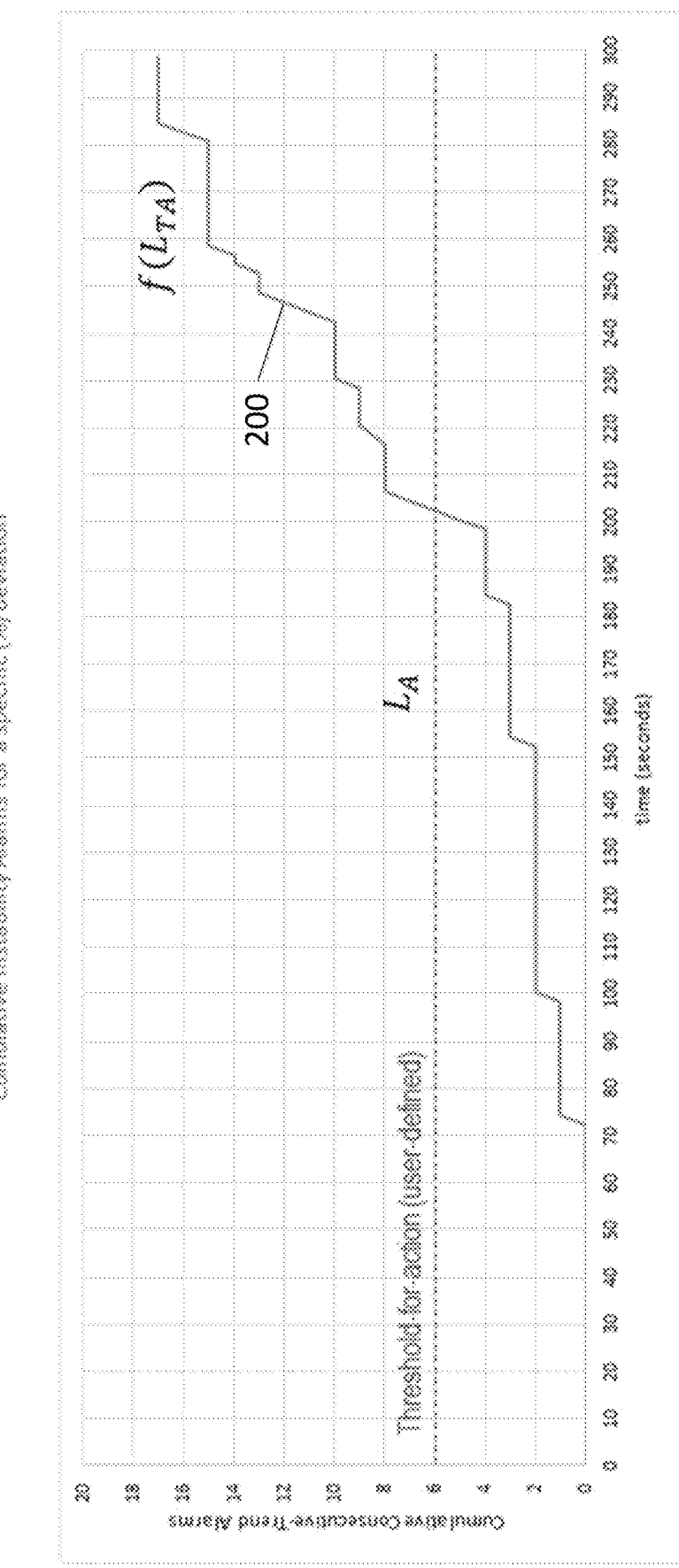
FIG. 5 is a graph of the cumulative stability alerts wherein a threshold-for-action based $L_A$, is defined for issuing a notification.

FIG. 5 plots the cumulative number of times these thresholds 158, 162 are exceeded, which reflects the accumulation of instability alerts in response to the signal data. In other words, the graph is the integrated or accumulated number of instability alert breaches obtained over time. The shape of the curve 200, $f(L_{TA})$, is a function of the number of the threshold deviations (i.e., $\pm L_{TA}$), the running average time interval, and the threshold on number of breaches that are acceptable during this running average time interval. The slope, growth rate, and maximum height of the curve depicted in this figure can vary. For instance, if the threshold deviation is increased, then the number of breaches per interval will decrease, and the height and slope of the curve in the depicted plot will flatten or decline. Hence, selecting the various contributing parameters such as the running average time interval, the number of acceptable occurrences of threshold breaches in a given time window, the threshold deviation value, and the number of acceptable occurrences of threshold breaches allowed to accumulate prior to communication of an instability alert to a frontline clinician, are all variables and subject to empirical validation. In practice, based upon a study of a population of patients within a telemetry unit over several months, it was determined that running average time intervals of 30 seconds, with threshold deviations of 30% and an expected number of threshold deviation occurrences of 5 or more tended to correlate well with the onset or issuing of physiologic monitor-based crisis alarms.

Figure 6:
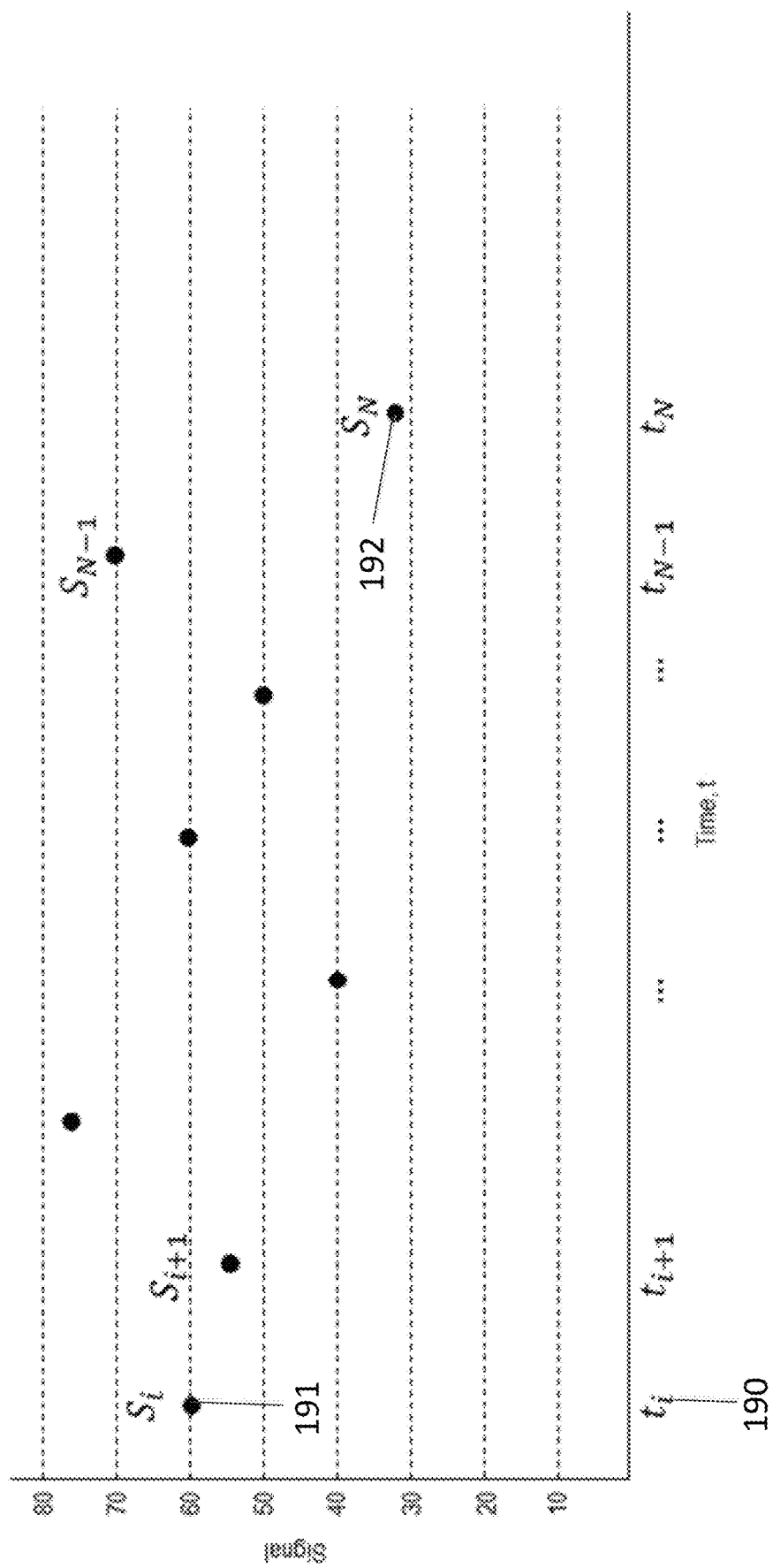
FIG. 6 is a scatter diagram depicting the discrete signal measurements that are used to compute the instability alert.
Figure 7:
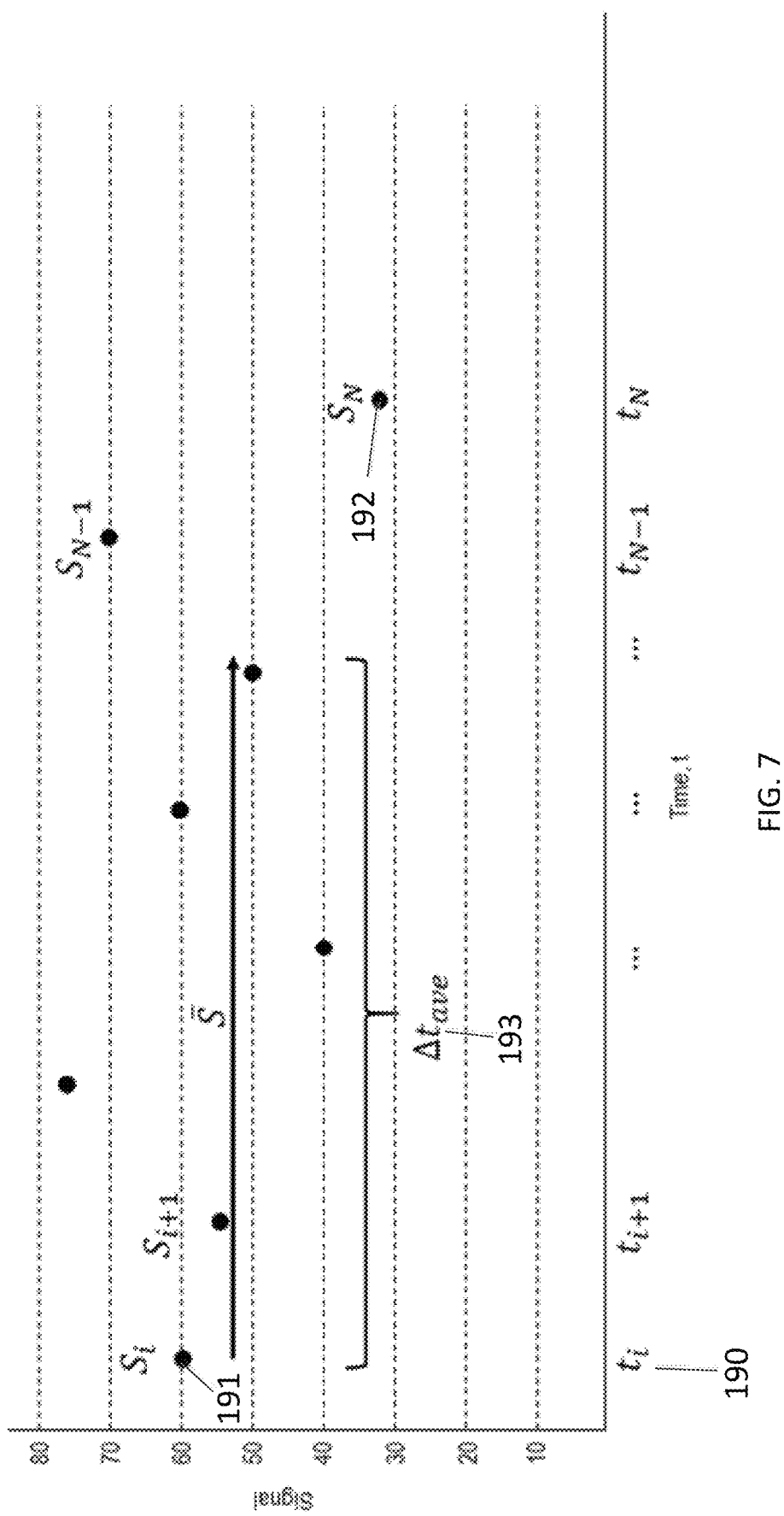
FIG. 7 depicts the discrete signal measurements of FIG. 6 with moving average calculated and overlaid on the signal measurements.

In more detail FIG. 6 illustrates the discrete measurements associated with a signal. Individual signals $S(t_i)$ at time $t_i$ 190, are described by the shorthand $S_i$ 191. A total of $S_N$ 192 signal measurements are represented, each at their respective time in the time series. As shown in FIG. 7, the signal measurements can be averaged using a moving average over a specific time window, $\Delta t_{ave}$ 193. This time window is represented as a dynamic sliding window that is updated with each measurement, i.

The signal running average over time is given by:

$$S_{ave_{i_e}} = \sum_{i=i_s}^{i=i_e} \frac{S_i}{N_i} \quad \text{Equation (1a)}$$

Where: $i_e$ is the ending interval for the averaging window;
$i_s$ is the starting interval for the averaging window;
$S_i$ is the signal measurement at each interval;
N is the quantity of measurements within the measurement window; and,
$S_{ave_{i_e}}$ is the running average signal measurement over the time interval $\Delta t_{ave}$.

Note that the time averaging window is given by:

$$\Delta t_{ave_{i_e}} = t_{i_e} - t_{i_s} \quad \text{Equation (1b)}$$

Where: $\Delta t_{ave_{i_e}}$ is the time averaging window;
$t_{i_e}$ is the time averaging window end time; and,
$t_{i_s}$ is the time averaging window start time.

Figure 8:
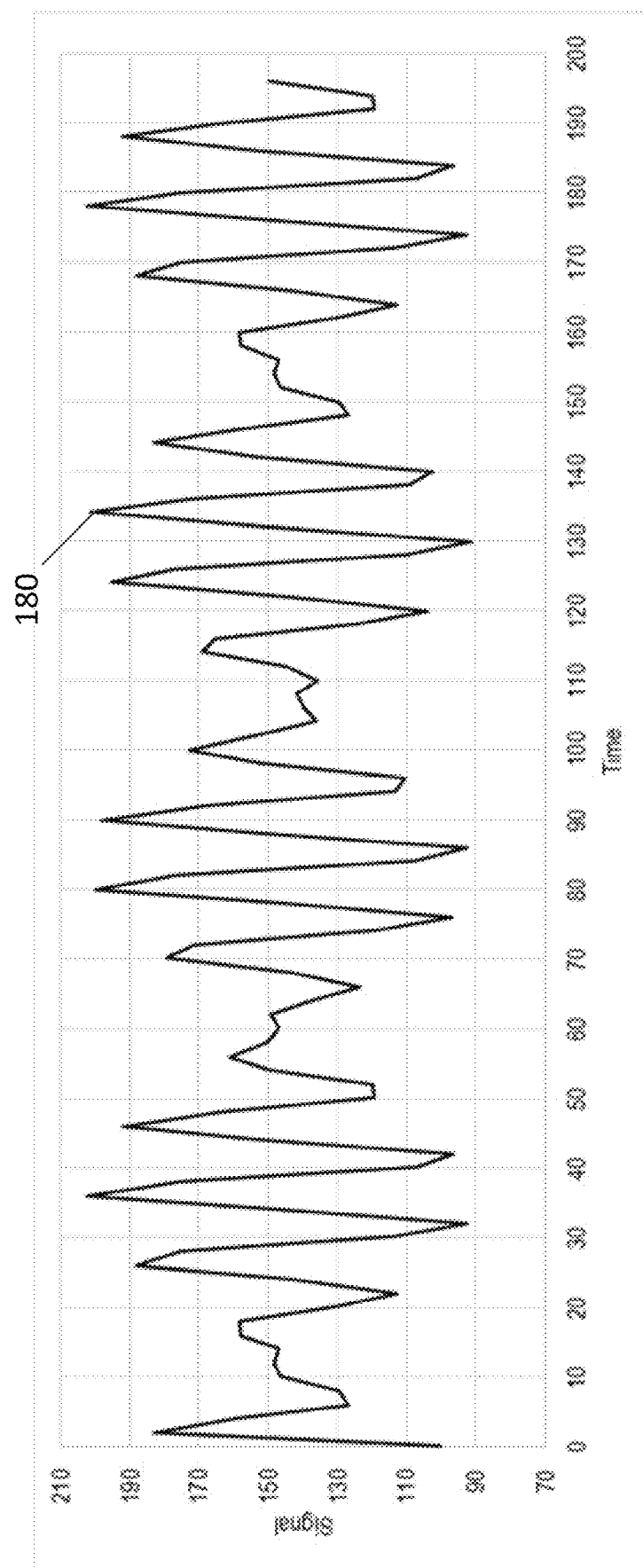
FIG. 8 is an example measurement signal.
Figure 9:
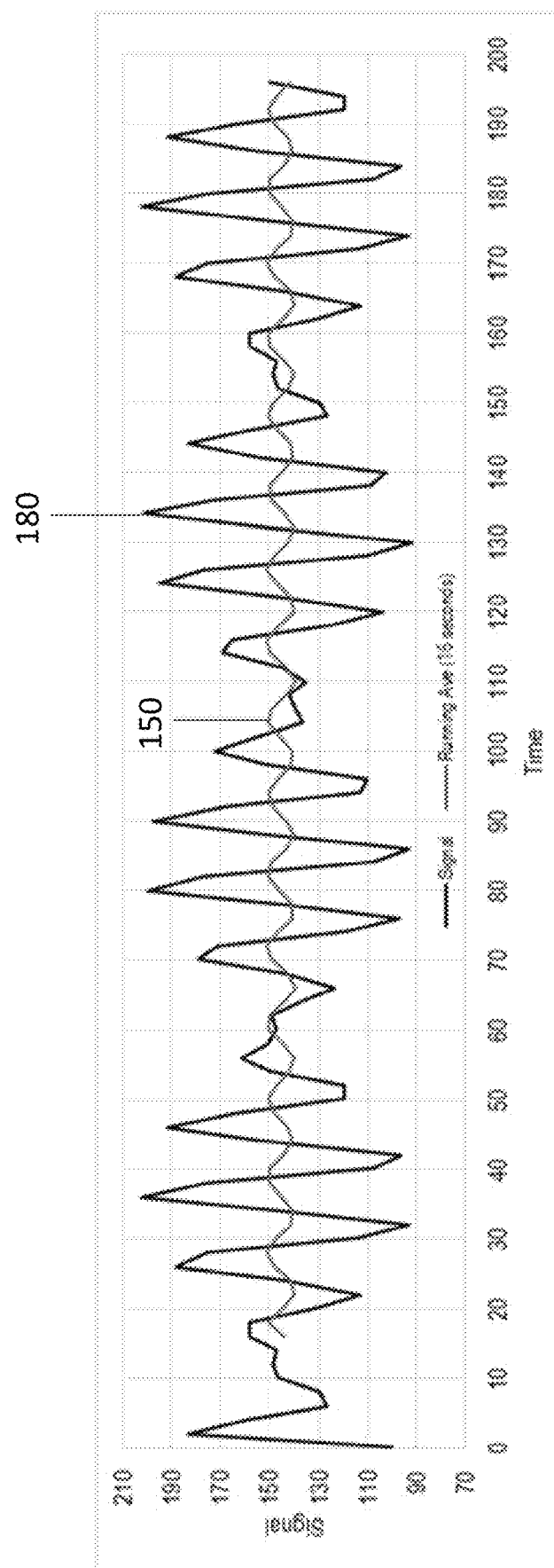
FIG. 9 is a plot of the signal of FIG. 8 with 16-second running signal average overlaid.

To illustrate this more clearly, an example signal is shown in FIG. 8. FIG. 9 depicts the same signal 180 with a running average, using a time averaging window, $\Delta t_{ave_{i_e}} = t_{i_e} - t_{i_s}$ of 16 seconds, overlaid on top of this signal. The time interval of 16 seconds was selected in this example for illustrative purposes and on the basis of the sampling interval. In this instance, in order to obtain a smooth running average, a minimum of 8 signal data points was selected. In one embodiment, the running average duration is set to anywhere from 8-20 times the sampling interval but may take on other values. The sample time averaging window is calculated as follows:

Next, in order to identify a significant signal deviation from this averaged signal 150. Upper threshold and lower threshold 158, 162 limits are established to determine what constitutes a significant signal deviation. This is accomplished by specifying a deviation threshold as a fraction of the average signal value as discussed previously. This deviation thresholds, $\pm L_{TA}$ from the average value, is typically less than 1 (100%) and empirically determined values range from 0.2-0.4, (20%-40%) with a nominal value of 0.3 for 30%. The signal deviation is measured with respect to both these high- and low-values. The high- and low-signal deviation thresholds 158, 162 which vary in time with each new measurement are fixed as they represent absolute deviations. Yet, the absolute value of the deviation can vary in time with each new measurement. For example, if the mean signal value is 30, then a 30% relative deviation would translate into an absolute deviation ±9. If the mean signal value is 40, then a 30% relative deviation would translate into an absolute deviation of 12. The high and low absolute signal deviations are given by the following:

$$S_{dh_{i}e} = S_{ave_{i}e} \times (1 + L_{TA}) \quad \text{Equation (2a)}$$

and, $$S_{dl_{i}e} = S_{ave_{i}e} \times (1 - L_{TA}) \quad \text{Equation (2b)}$$

Figure 10:
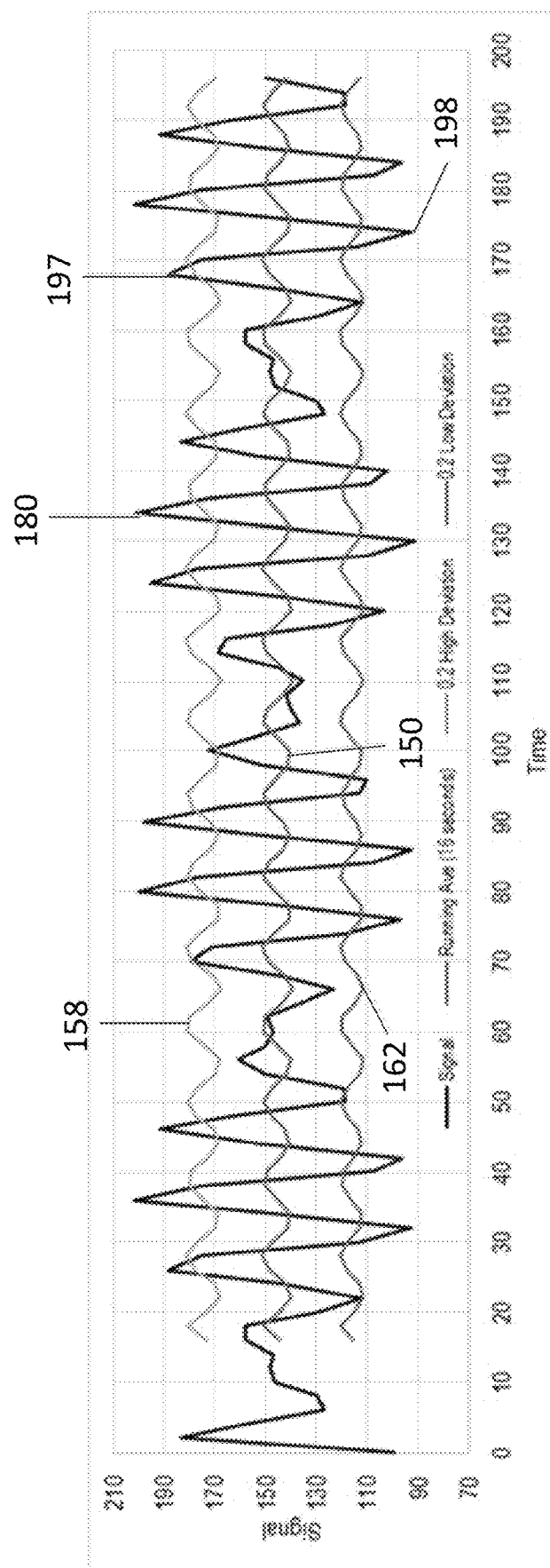
FIG. 10 depicts the measurement signal of FIG. 9 including a running signal average, and high-low signal deviations based on a signal deviation threshold of 0.2.

Where: $S_{dh_{i}e}$ is the high absolute signal deviation;
$S_{dl_{i}e}$ is the low absolute signal deviation;
$S_{ave_{i}e}$ is the average signal deviation, FIG. 10 illustrates the above equations relative to the example signal waveform of FIG. 8. FIG. 10 graphs the high-and low-signal deviations 158, 162 overlaid with the sample times. The signal measurements can be seen emerging beyond the high and low values at various points along the time series. The location or areas where the signal breaches or exceeds the high or low threshold 197, 198 are counted as binary values of "1" indicating whether these breaches are above- or below-upper or lower thresholds, respectively. For the embodiment presented here, breaches of the thresholds are treated as binary (i.e., the same for slight versus large breaches). Yet, variations in size of the threshold breach can be taken into account by associating the amount of the threshold breach with increases in the relative weight of the breach. For example, a deviation in excess of one deviation threshold would be counted as "1"; a deviation of 2× one deviation threshold would be counted as "2" and so on. The selection of the amount of deviation is made empirically and based on the scope of the studies thus far, a binary value of "0" or "1" has appeared adequate and shown high correlations with crisis alarm onset.

Figure 11:
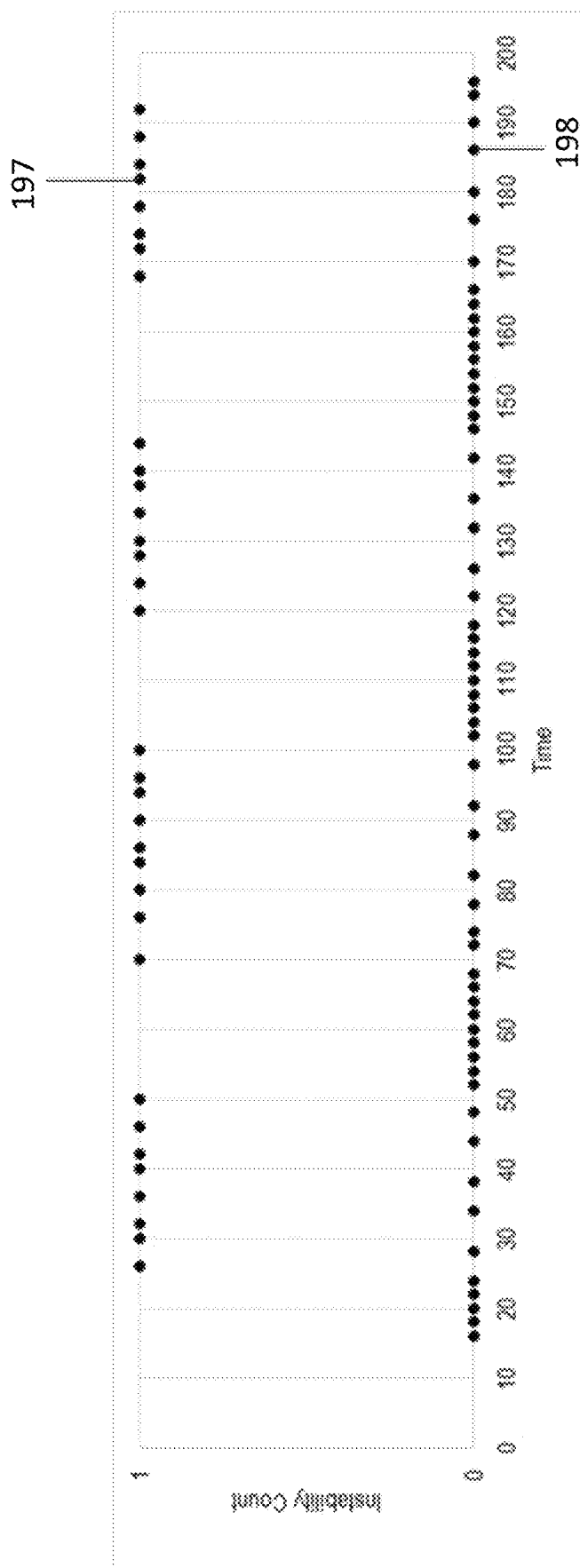
FIG. 11 depicts signal deviation threshold, or instability, counts indicating points in time in which the measurement signal breaches the high-or-low-signal deviation.

A raw plot of the signal deviations is shown in FIG. 11 for the case of the signal and deviation thresholds 158, 162 presented in FIG. 10. The plot in FIG. 11 identifies points where the signal thresholds are breached by the measurement signal (example 197, 198). These breach events, $In_i$, are valued as follows:

$$In_i=1 \text{ if breach, or} \qquad \text{Equation (3a)}$$

$$In_i=0 \text{ otherwise} \qquad \text{Equation (3b)}$$

Where: $In_i$ is the instability threshold breach ("In") at time instant i.

Figure 12:
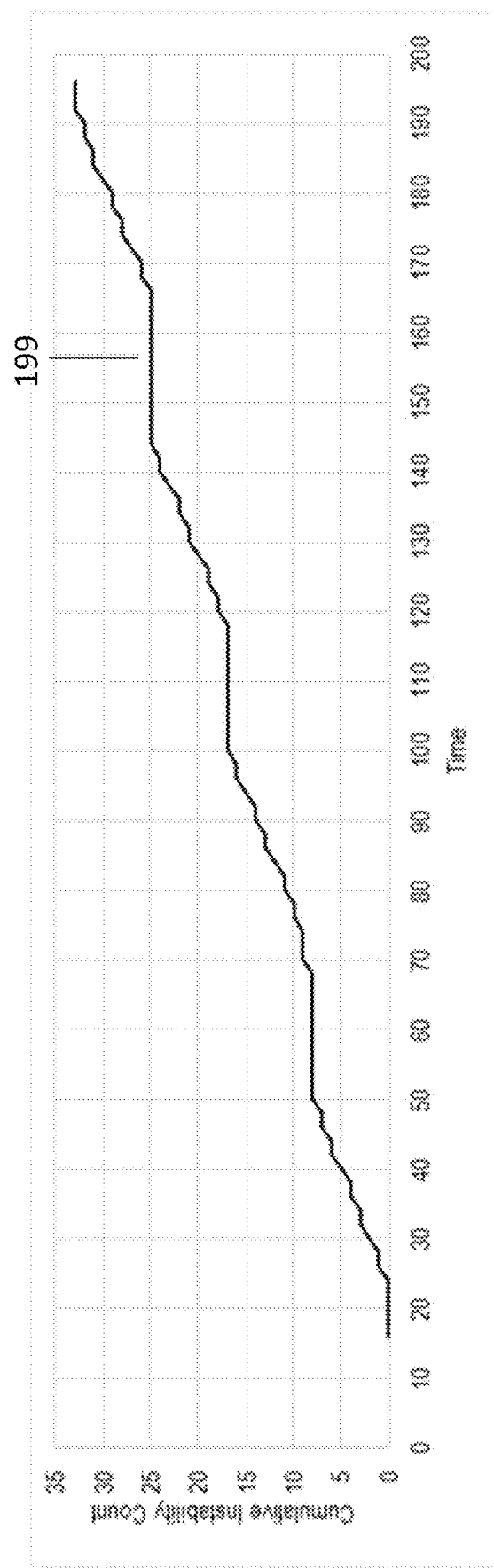
FIG. 12 plots cumulative signal deviations, or cumulative instability counts of FIG. 11.

The summation or integral of all signal deviations ($I_{I_N}$) 199 is represented in the plot of FIG. 12.

Figure 13:
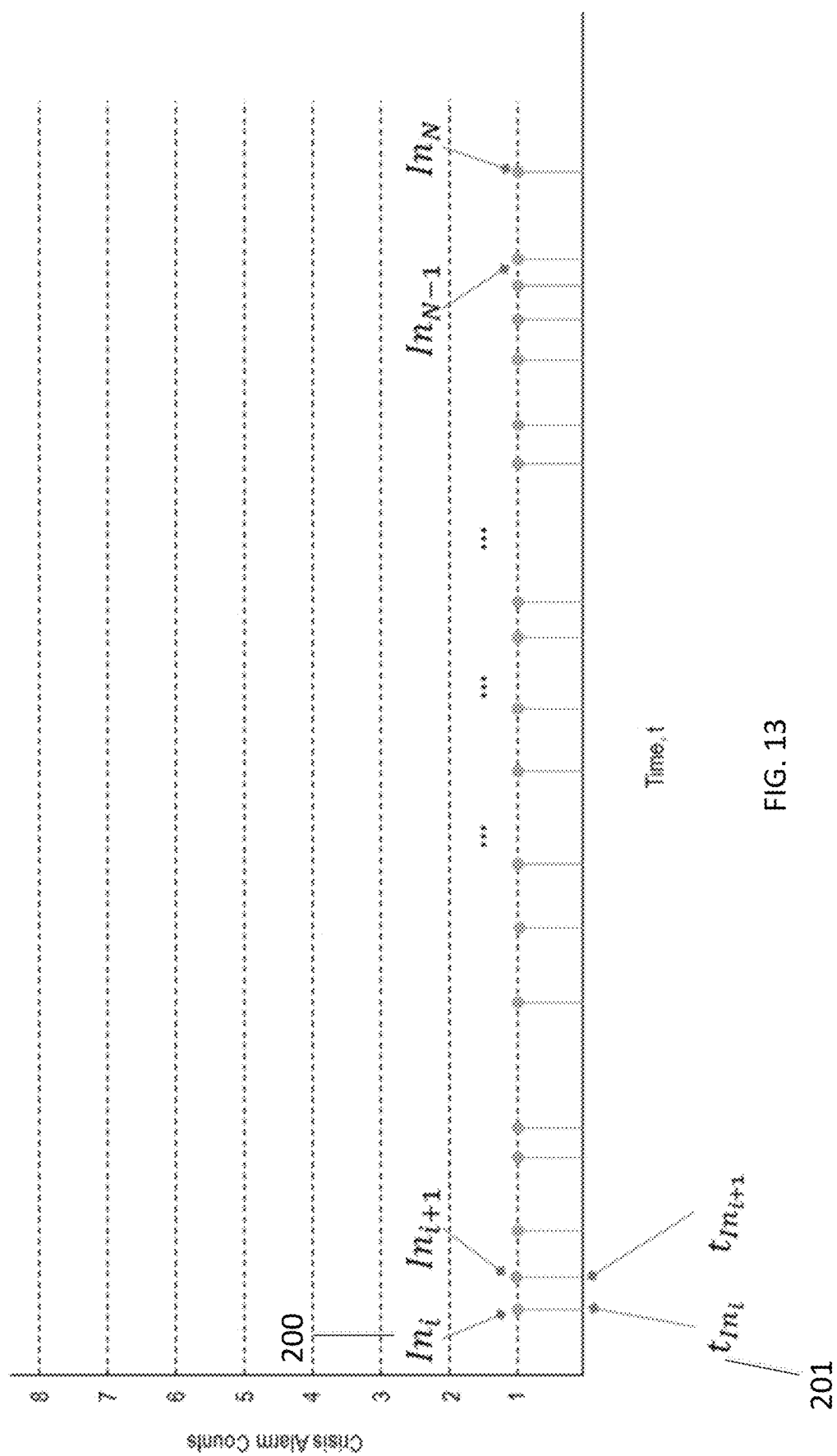
FIG. 13 illustrates the individual signal threshold breaches, or instability counts, at discrete points in time. This plot differs from FIG. 11 in that it illustrates more closely individual threshold breaches and assigns notation associated with the consecutive instances of these occurrences.
Figure 14:
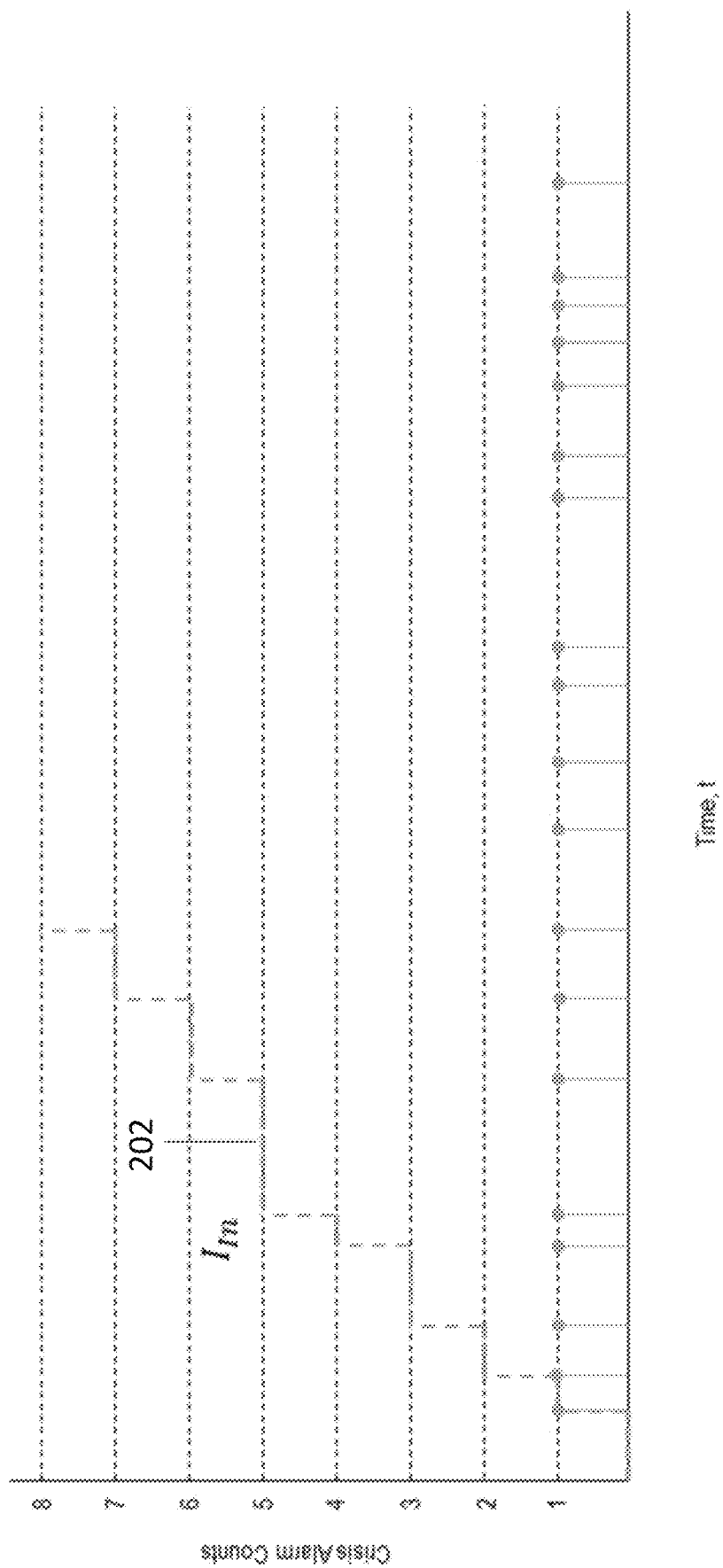
FIG. 14 depicts integrated or cumulative number of instability threshold counts or breaches.

The quantity of cumulative breaches per some unit time frame is also significant. If the individual threshold breaches, also called instability events ($In_i$) 200, are plotted as a "1" against the time of the event ($t_{In_i}$) 201 the plot in FIG. 13 is formed. FIG. 13 describes more details than FIG. 11, and identifies what is meant by occurrences of the instability breaches, $I_n$, for the purpose of the mathematical development, whereas FIG. 11 shows simply the instability breaches determined for the worked sample problem. The integral or sum of these individual breaches 202 is given by equation 4:

$$I_{I_N}=\Sigma_{i=0}^{i=N} In_i \qquad \text{Equation (4)}$$

and is shown in FIG. 14.

One can also define a metric of the number of cumulative breaches for some unit of time ($\Delta t_{es}$) This time frame established an epoch over which the integrated breaches given by Equation (4) are "counted" or accumulated, and defines a rate of accumulation. This metric is given by the following expression:

$$\dot{I}_{In}(\Delta t_{es}) = \frac{\sum_{i=i_s}^{i=i_e} In_i}{\Delta t_{es}} \qquad \text{Equation (5)}$$

Figure 15:
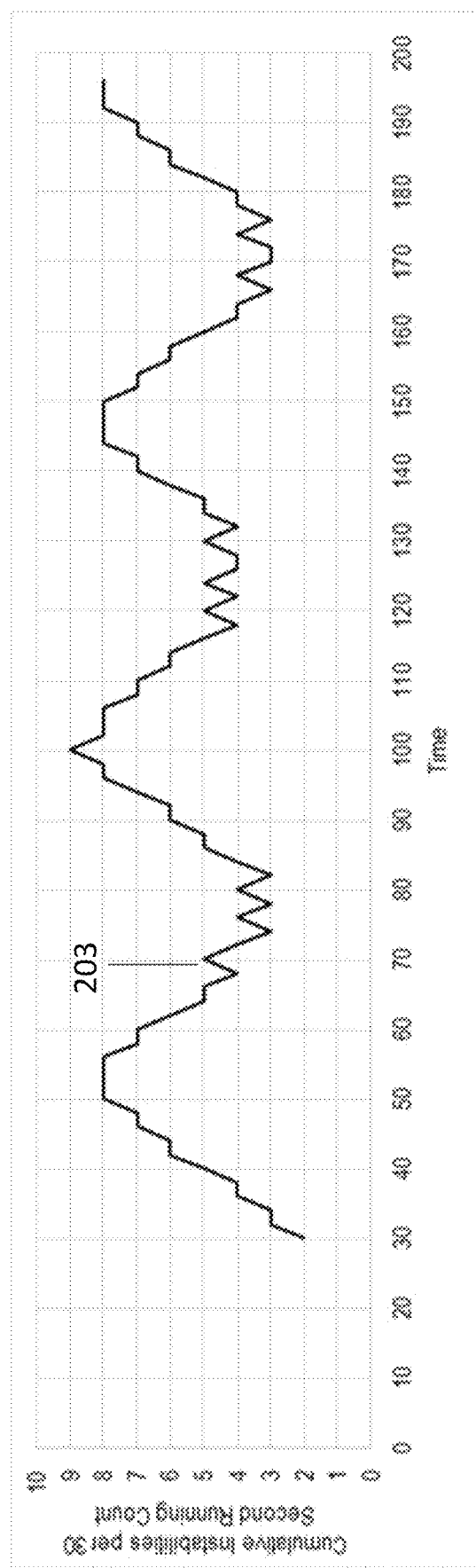
FIG. 15 is a plot of cumulative instability counts or breaches versus time for a specific cumulative running time window.

Where:

$$\Delta t_{es}=t_{i_e}-t_{i_s} \qquad \text{Equation (6)}$$

and $\dot{I}_{In}(\Delta t_{es})$ is the rate of accumulation over this interval. FIG. 15 shows the plot of Equation (5) 203 for the sample data presented in FIG. 12.

It is possible to adjust the sensitivity of the instability alerts by reporting only when, say, the quantity of instability alerts grows to some number and thereafter a multiple of that number. A reason for doing this is to decrease the overall quantity of alerts issued to frontline clinicians by decreasing the sensitivity of the alert. In a study of patients in a telemetry unit over a period of 3 months, it was observed that issuing of instability alerts when the cumulative quantity grew to larger than 5 within a given time window, then report to frontline clinicians. The effect was identification of the pending onset of crisis alarms, with early onset identification ranging from minutes to several hours before the actual occurrence of a crisis alarm. The benefit to the patient is providing the forewarning to clinical of an impending crisis alarm that can then be assessed and mitigated. Thus, if the value of Equation (4) exceeds, say, 5, then issue an alert notification. Once the breach occurs, repeat the alert notification if the value of Equation (4) again exceeds this threshold and repeat as necessary. Mathematically, $$\text{If } I_{I_N} > 5 \text{ then, reset instability counts and notify.} \qquad \text{Equation (6)}$$

Figure 16:
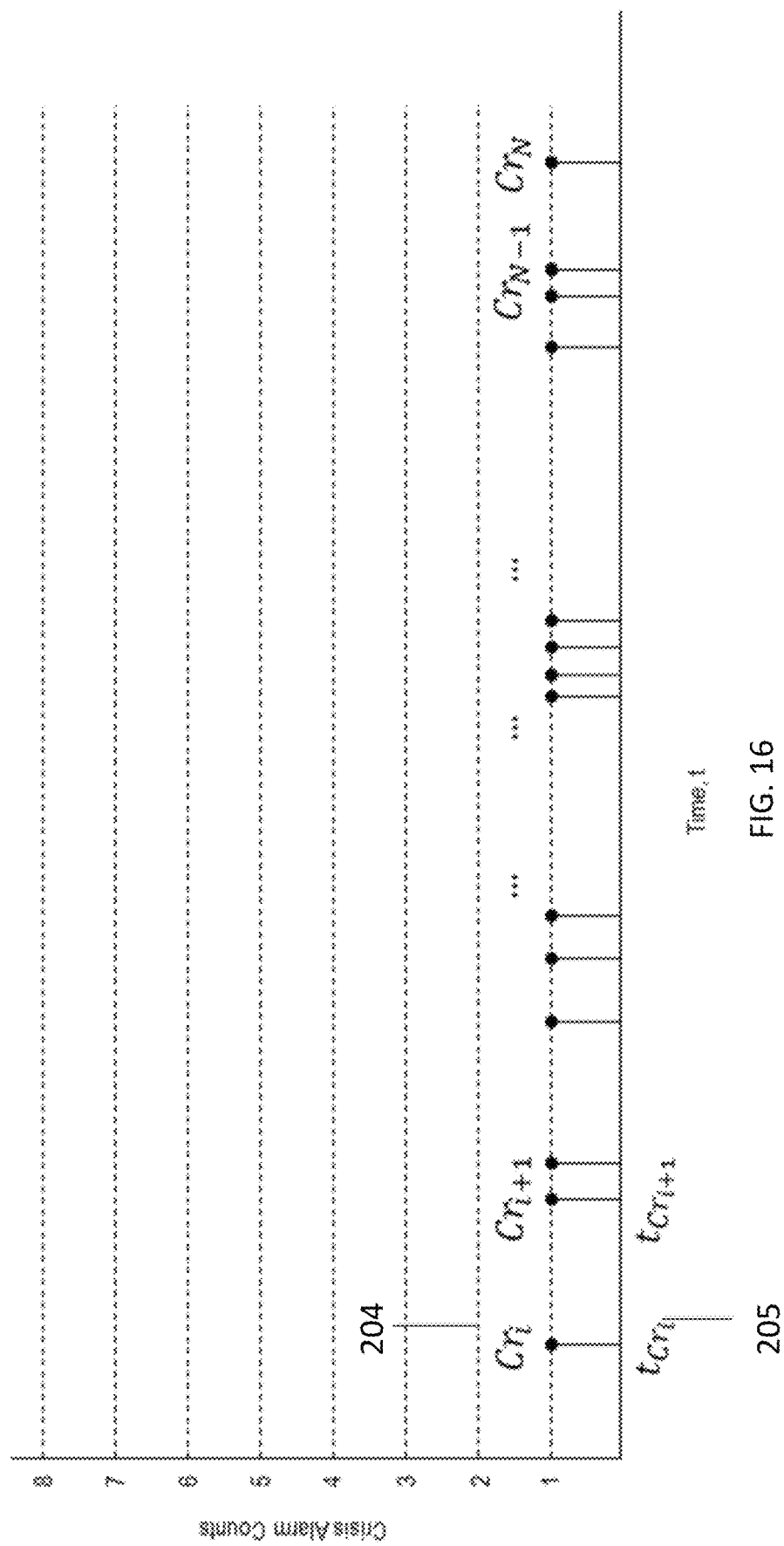
FIG. 16 depicts individual instances of crisis alarms as issued by the telemetry monitoring equipment.
Figure 17:
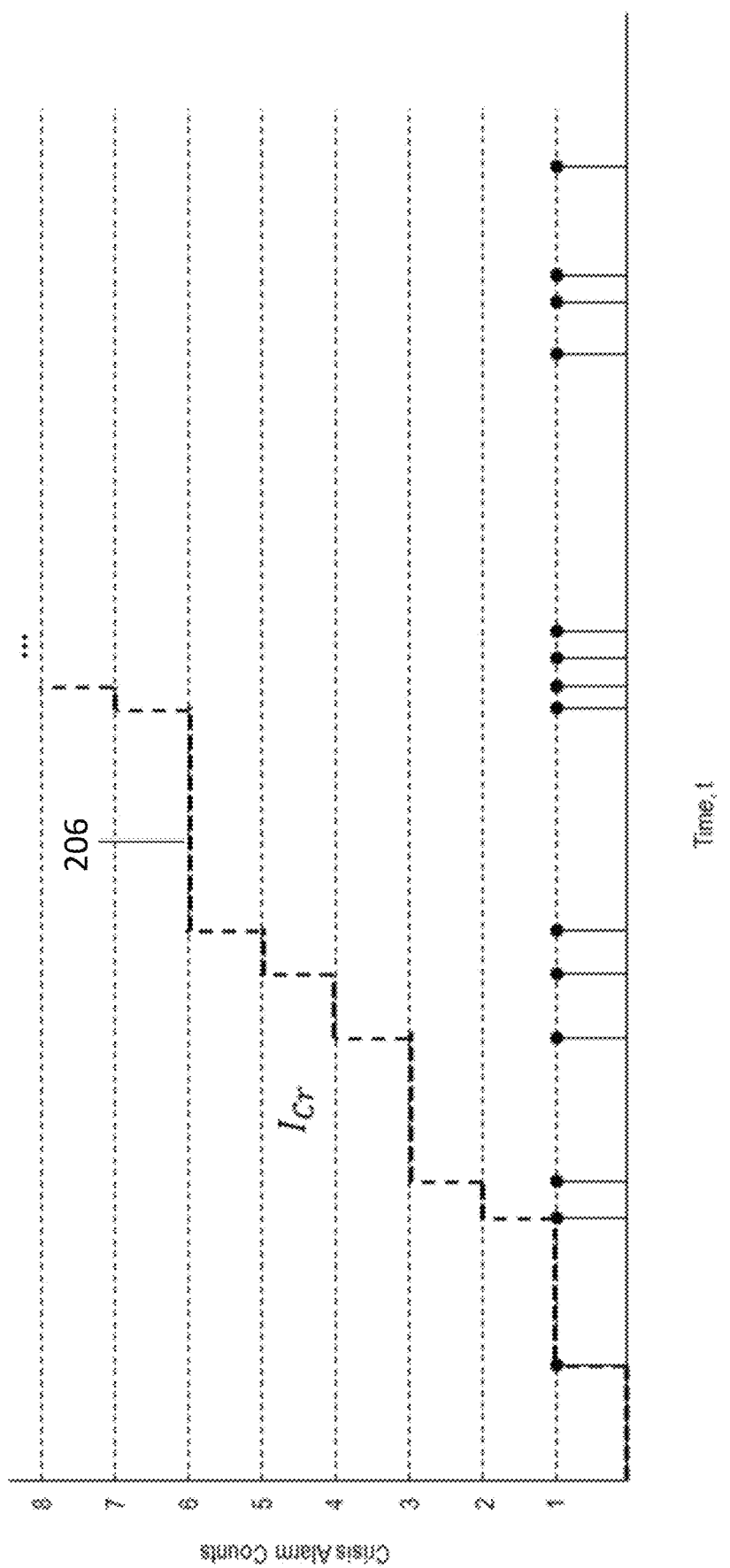
FIG. 17 depicts cumulative crisis alarms, which is the integral of the individual crisis alarms. The term integration and summation are used interchangeably in that, for discrete data elements, integration is approximated by a Riemann sum of the individual discrete data elements. Integration is taken to mean to be taken over infinitesimally small increments, dt. In the case presented here and in discussions regarding integration in this disclosure, integration is taken to mean the discrete summation or accumulation of individual contributing data elements over time.

Crisis alarms are accumulated in a similar manner. FIG. 16 and FIG. 17 are directly analogous to FIG. 13 and FIG. 14, respectively, but with the focus on crisis alarms that are telemetry-monitor-issued. The integrated crisis alarm instances are accumulated in like manner as the instability breaches, per Equation (4), by substituting the crisis alarms for the instability breaches. In FIG. 16, the individual crisis alarms also ($Cr_i$) 204 are plotted as a "1" against the time of the event ($t_{Cr_i}$) 205. The integral or sum of these individual alarms 206 is given by FIG. 17.

Figure 18:
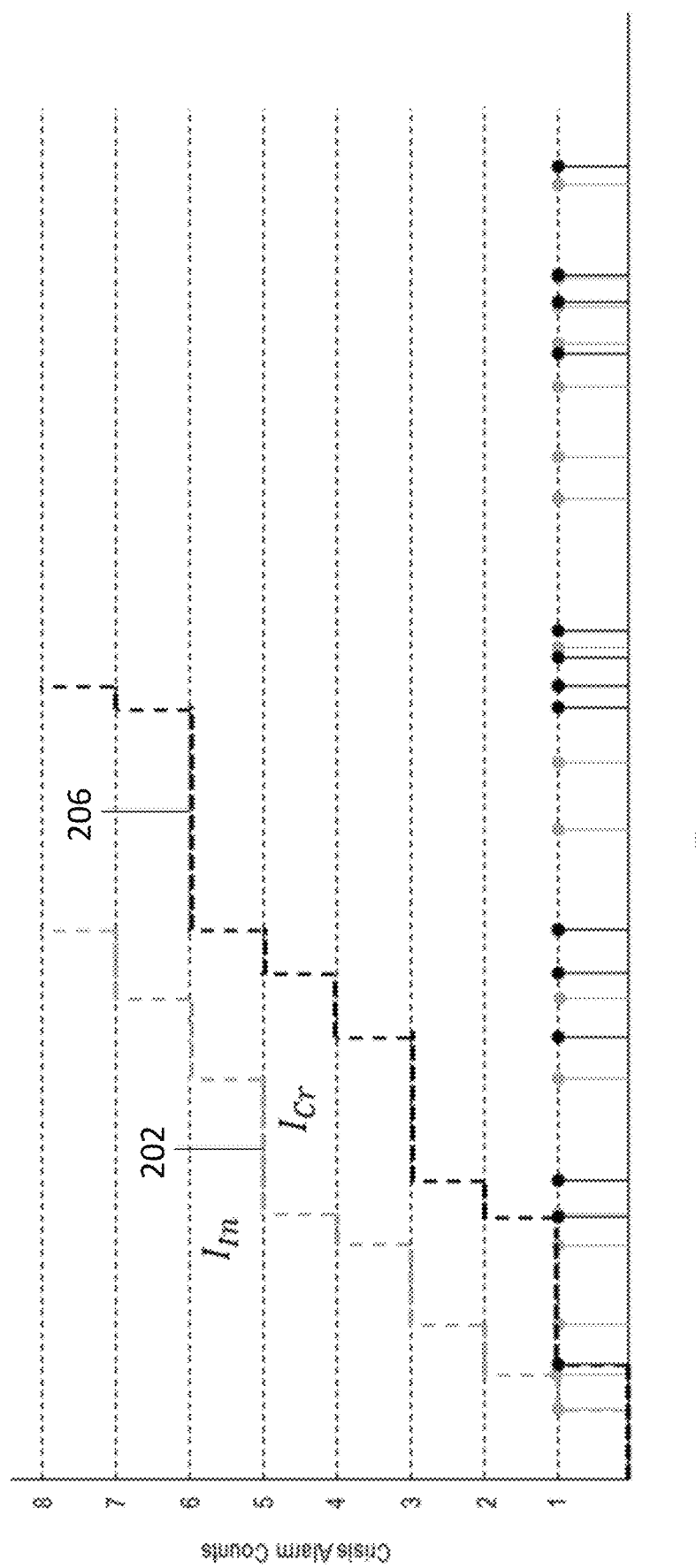
FIG. 18 is a plot of both cumulative crisis alarms and instability counts or breaches on the same axes.

Now, both the cumulative instability breaches 202 and the crisis alarms 206 can be plotted on the same axes, and a qualitative illustration of this is provided in FIG. 18. These two time series can be evaluated in terms of cross-correlation to establish the power and the direction of the relationship. This is done using the covariance of the two series. The sample covariance is calculated as follows:

$$\text{Cov}(In, Cr) = \frac{\sum_{i=0}^{i=N}(I_{In_i} - \langle I_{In}\rangle)(I_{Cr_i} - \langle I_{Cr}\rangle)}{N-1} \qquad \text{Equation (7)}$$

where the bracketed < >quantities represent the mean values.

The sample correlation between instability and crisis is then given by:

$$r_{IC} = \frac{\text{Cov}(In, Cr)}{S_{In} \times S_{Cr}} \qquad \text{Equation (8)}$$

where $S_{In}$ and $S_{Cr}$ are the sample standard deviations of the instabilities and the crisis alarms, respectively. A value of 1.0 indicates perfect correlation between instability ($I_n$) and crisis (Cr). A value of 0 represents no correlation. A value of −1 indicates perfect inverse correlation between instability ($I_n$) and crisis (Cr).

Figure 19:
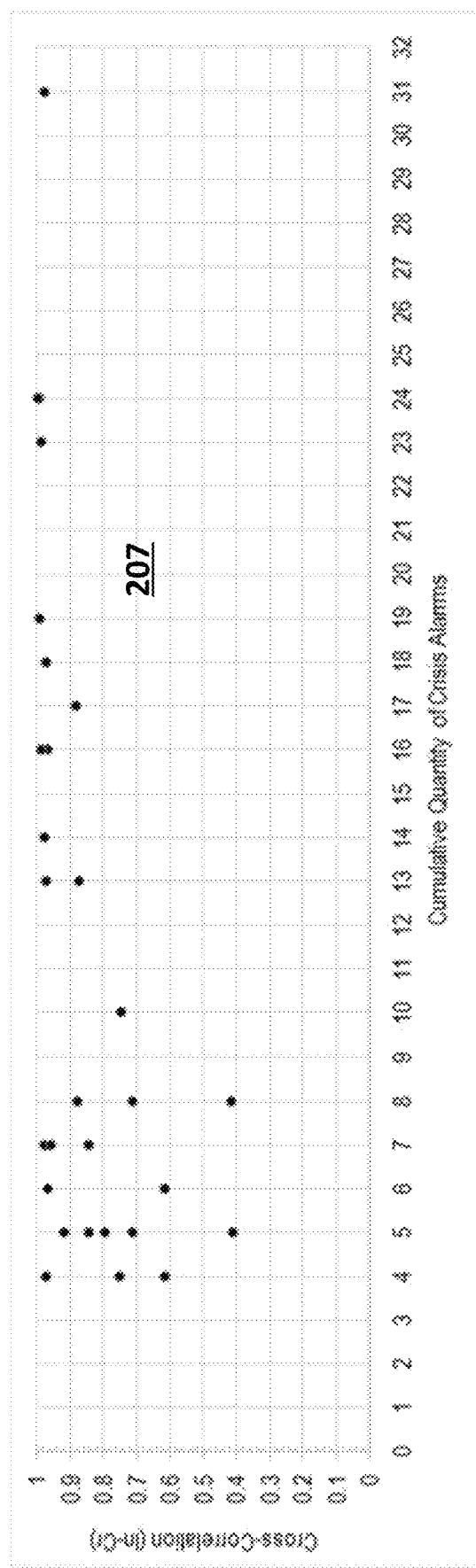
FIG. 19 charts the cross-correlations between cumulative instability counts or breaches and crisis alarms across in a telemetry unit.

EXAMPLE A study was conducted using samplings of 20 patients over 30 days and 20 patients over 5 days. A total of 1300 machine-issued crisis alarms were received on this population during the study interval. A subset of these patients experiencing crisis alarms were extracted and evaluated using the above methodology. The cross correlations of instabilities and crises were calculated using Equation (8) and the preceding methodology. The cross-correlation 207 is presented in FIG. 19.

The total number of bed locations multiplied by the total number days of continuous monitoring at those locations is termed "location-days". For instance, telemetry monitoring in a single unit involved data collection over 30 days (i.e., 24 hours per day) in 20 specific telemetry locations. All locations were populated at or near 100% consensus during this period. Hence, the total quantity of "location-days" of monitoring was 20×30=600, or 600 separate 24-hour periods of continuous telemetry data.

The cross-correlations are in excess of 0.9 when crisis alarm quantities are >10. Average cross-correlation for all samples together is 0.85. The time averaging was calculated according to Equation (1a). A 30-second sample average was used for the running average, per Equation (1b), and a sample deviation threshold of 0.3 was used, per Equations (2a, b).

Figure 20:
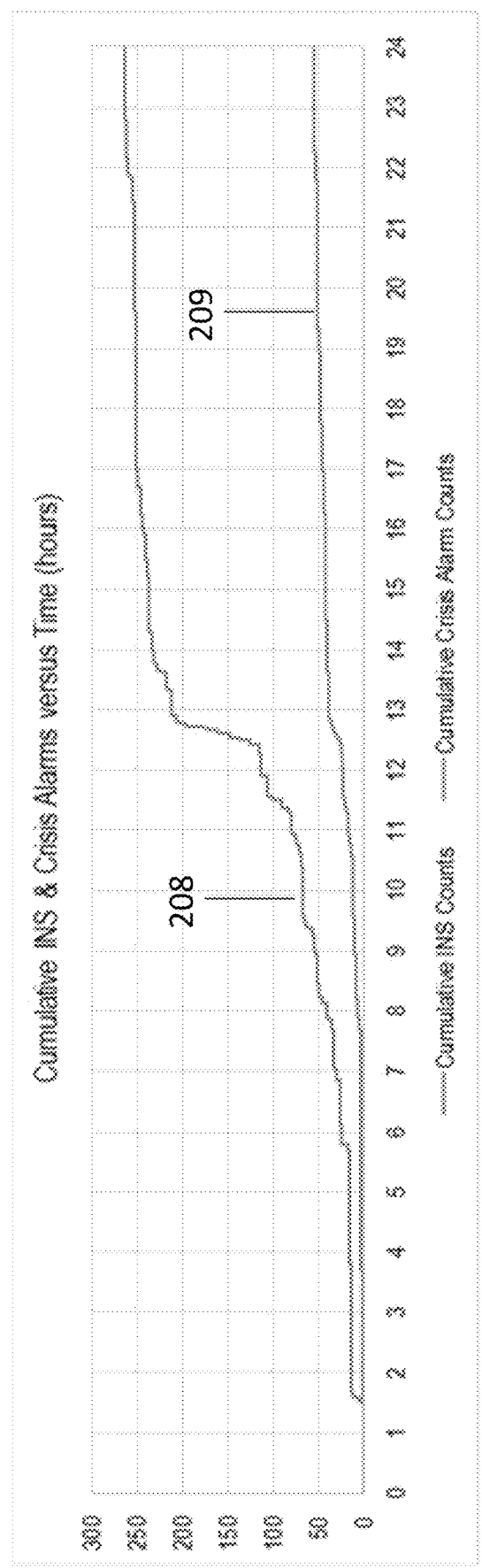
FIG. 20 illustrates the cumulative instability alerts and crisis alarm quantities versus time in hours.
Figure 21:
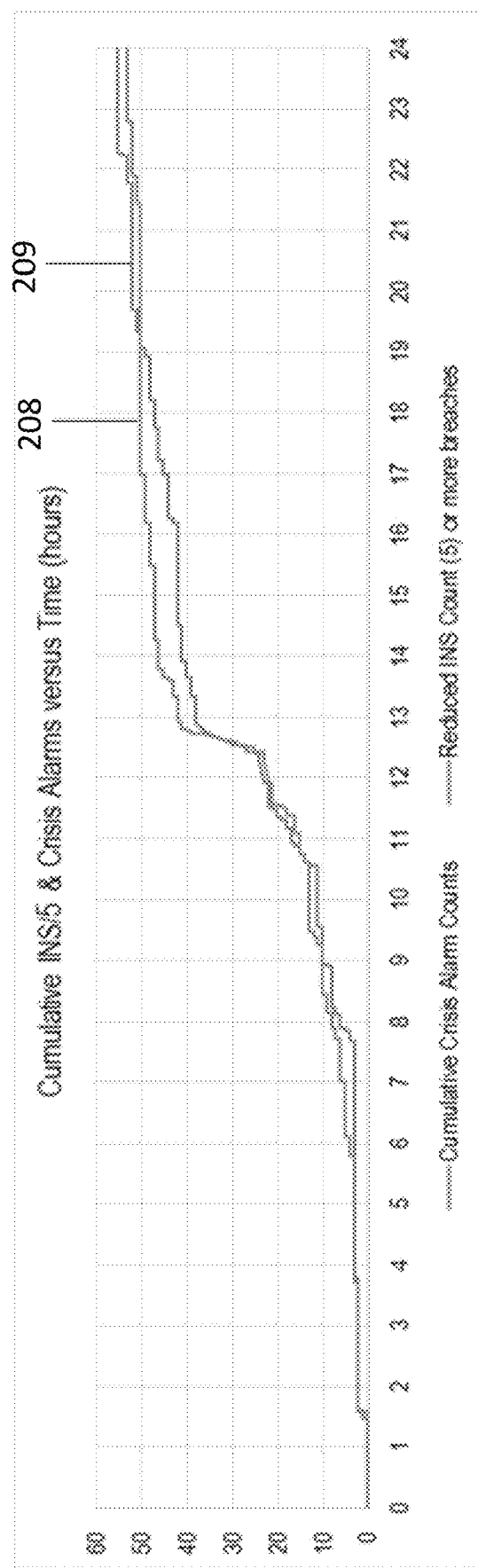
FIG. 21 depicts cumulative instability and crisis alarm quantities over time with the imposition that instability counts are not triggered until at least 5 are accumulated.

FIG. 20 depicts the cumulative instability 208 and crisis quantities 209 for one patient. FIG. 21 plots the same results of the cumulative instability 208 and crisis quantities 209 for one patient when a 5-breach threshold limit is imposed on the instability counts as the threshold at which clinical staff is to be informed of an impending event. The matchup of the two curves in FIG. 20 and FIG. 21 show the strong correlation between these two curves at a sample deviation of 0.3 is 0.993.

Figure 22:
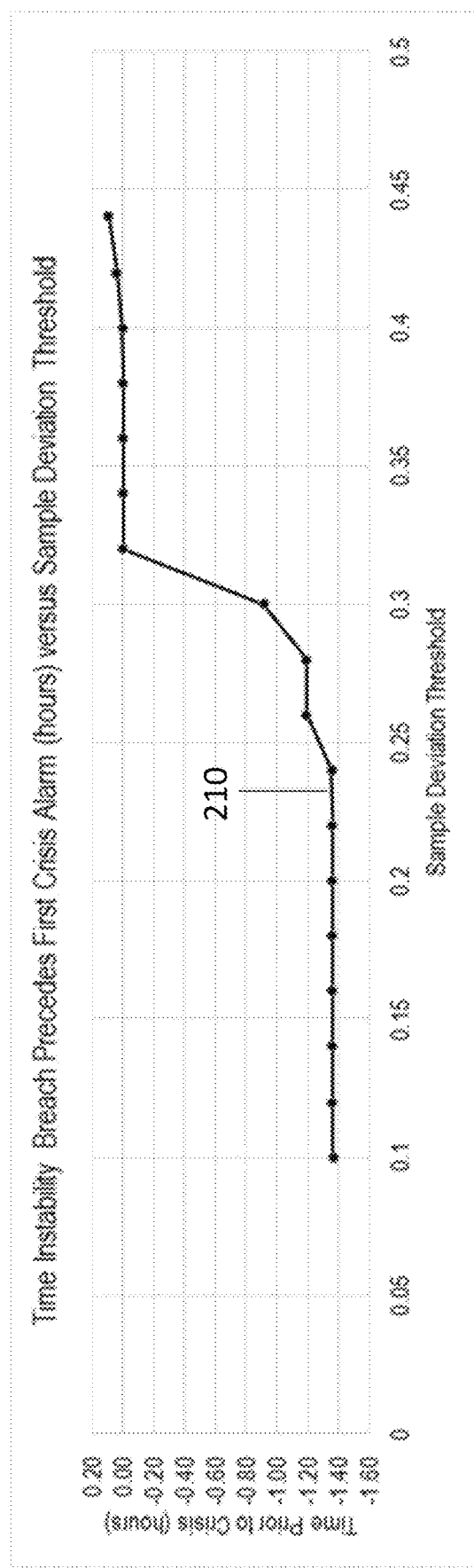
FIG. 22 depicts the time of 5 Instability breaches prior to a first crisis alarm.

A key observation is also the amount by which the instabilities precede the actual issuing of a crisis alarm. For the patient presented in FIG. 21, the plot in FIG. 22 plots the time prior to the crises against sample deviation threshold. The implication is that the cumulative quantity of instability alerts correlate with the cumulative quantity of crisis alarms issued from the telemetry monitors. When a reporting threshold of 5 instability threshold breaches was applied before a notification was issued, the instability alerts correlate visually with the onset of crisis alarms. This is somewhat intuitive as the variability in heart rate, inclusive of signal artifact, also tends to precede the onset of crisis alarms.

FIG. 22 indicates, as a demonstration to a single patient, at a sample deviation threshold of 0.3, a breach threshold of 5 instability notifications 210 is identified approximately 1 hour prior to the issuing of the first crisis alarm. Hence, from a surveillance perspective, the instability breach count ("Instability Surveillance Calculation") can provide an early indicator of an impending event, or of the need to address a significant level of discrete heart rate variability. This indicates that the instability alert predated the occurrence of the initial crisis alarm on this patient and, from the population of patients, the instability alert was a good indicator that a crisis alarm was likely on a patient, with an average correlation of 0.85.

FIG. 23 is a flowchart of the described method, assuming an operational environment in which pre-adjusted limits are established and used. When training to determine the optimal upper and lower limit thresholds and the running average time, this exercise involves parameterizing these values to determine the number of issued instability alerts for a given department or unit. For example, when applying to a telemetry unit, the default or offered set of values might be a running average interval of 30 seconds and an upper and lower relative limit threshold of 30%. As the system is evaluated in the live environment, adjustments to these parameters are made as required in order to reduce the overall number of issued instability alerts and to increase the specificity of the response to the particular patient population. The flowchart describes the general process flow associated with running the algorithm within an existing environment.

First, the system continuously or discretely measures a patient's physiologic signal 301. In this instance, the physiologic signal is heart rate. The system calculates a running average to establish a signal baseline over a time interval 302. Upper and lower limit thresholds are the defined with respect to the running average based on past history or clinician selection 303. When the measurement exceeds the average trend line by either a positive or negative amount, it is noted as a threshold breach 304. The cumulative number of breaches is noted to determine the accumulation of instability alerts 305. If the number of breach events is high, then the system determines whether a crisis alarm must be emitted 306. The system outputs a crisis alarm signal to a clinician to take action 307.

Unless specifically stated otherwise as apparent from the following discussion, it is appreciated that throughout the description, discussions utilizing terms such as "processing" or "computing" or "calculating" or "delaying" or "comparing", "generating" or "determining" or "forwarding or "deferring" "committing" or "interrupting" or "handling" or "receiving" or "buffering" or "allocating" or "displaying" or "flagging" or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The algorithms presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language, and various embodiments may thus be implemented using a variety of programming languages.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

The examples presented herein are intended to illustrate potential and specific implementations of the present disclosure. The examples are intended primarily for purposes of illustration of the invention for those skilled in the art. No particular aspect or aspects of the examples are necessarily intended to limit the scope of the present invention.

The figures and descriptions of the present invention have been simplified to illustrate elements that are relevant for a clear understanding of the present invention, while eliminating, for purposes of clarity, other elements. Those of ordinary skill in the art may recognize, however, that these sorts of focused discussions would not facilitate a better understanding of the present disclosure, and therefore, a more detailed description of such elements is not provided herein.

The processes associated with the present embodiments may be executed by programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary.

Computer systems and computer-based devices disclosed herein may include memory for storing certain software applications used in obtaining, processing, and communicating information. It can be appreciated that such memory may be internal or external with respect to operation of the disclosed embodiments. The memory may also include any means for storing software, including a hard disk, an optical disk, floppy disk, ROM (read only memory), RAM (random access memory), PROM (programmable ROM), EEPROM (electrically erasable PROM) and/or other computer-readable memory media. In various embodiments, a "host," "engine," "loader," "filter," "platform," or "component" may include various computers or computer systems, or may include a reasonable combination of software, firmware, and/or hardware.

In various embodiments of the present disclosure, a single component may be replaced by multiple components, and multiple components may be replaced by a single component, to perform a given function or functions. Except where such substitution would not be operative to practice embodiments of the present disclosure, such substitution is within the scope of the present disclosure. Any of the servers, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it may be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present disclosure. Programming languages for computer software and other computer-implemented instructions may be translated into machine language by a compiler or an assembler before execution and/or may be translated directly at run time by an interpreter.

Examples of assembly languages include ARM, MIPS, and x86; examples of high level languages include Ada, C, C++, C#, COBOL, Fortran, Java, Lisp, Matlab, Pascal, Object Pascal, Swift, Visual Basic; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium. Thus, the operation and behavior of the embodiments are described without specific reference to the actual software code or specialized hardware components. The absence of such specific references is feasible because it is clearly understood that artisans of ordinary skill would be able to design software and control hardware to implement the embodiments of the present disclosure based on the description herein with only a reasonable effort and without undue experimentation.

Various embodiments of the systems and methods described herein may employ one or more electronic computer networks to promote communication among different components, transfer data, or to share resources and information. Such computer networks can be classified according to the hardware and software technology that is used to interconnect the devices in the network.

The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods, systems, and tools described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity.

Unless otherwise indicated, all numbers expressing lengths, widths, depths, or other dimensions and so forth used in the specification and claims are to be understood in all instances as indicating both the exact values as shown and as being modified by the term "about." As used herein, the term "about" refers to a ±10% variation from the nominal value. Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Any specific value may vary by 20%.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

It will be appreciated by those skilled in the art that various modifications and changes may be made without departing from the scope of the described technology. Such modifications and changes are intended to fall within the scope of the embodiments that are described. It will also be appreciated by those of skill in the art that features included in one embodiment are interchangeable with other embodiments; and that one or more features from a depicted embodiment can be included with other depicted embodiments in any combination. For example, any of the various components described herein and/or depicted in the figures may be combined, interchanged, or excluded from other embodiments.

What is claimed is:

1. A method for creating alarm signals based on time-series signal behavior of real-time discrete data obtained from a medical device comprising:
    continuously monitoring a patient's clinical reading via data obtained from the medical device;
    continuously calculating and updating a current running average over a defined time interval of the data obtained from the medical device based on a predetermined running average time interval window, wherein the calculated current running average varies over time;
    continuously setting a current upper and a lower limit threshold for the clinical reading in response to the calculated current running average, wherein the current set upper limit threshold and/or the current set lower limit threshold varies over time;
    determining, over a predetermined monitoring time period, one or more breaches of at least one of a current set upper limit threshold and a current set lower limit threshold, wherein each breach is a breach event;
    calculating, over the predetermined monitoring time period, the total number of breach events for at least one of the upper limit threshold and the lower limit threshold;
    issuing an alarm when the calculated total number of breach events for at least one of the upper limit threshold and the lower limit threshold exceeds a predetermined breach event threshold; and
    calculating a change in at least one of the upper and lower limit thresholds when the calculated total number of breach events exceeds a predetermined amount.

2. The method of claim 1, wherein a new upper limit threshold and a new lower limit threshold in subsequent defined time intervals are in response to a percentage of the running average, representative of a normal range of variability associated with measurements of a specific patient.

3. The method of claim 2, wherein the percentage is between 10% and 30% inclusive.

4. The method of claim 1, further comprising:
    identifying time points corresponding to the breaches of the upper and lower limit threshold; and
    determining a quantity of cumulative breaches based on a time frame.

5. A method for creating alarm signals based on time-series signal behavior of real-time discrete data obtained from a medical device comprising:
    continuously monitoring a patient's clinical reading via data obtained from the medical device;
    continuously calculating and updating a current running average over a defined time interval of the data obtained from the medical device based on a predetermined running average time interval window, wherein the calculated current running average varies over time;
    continuously setting a current upper and a lower limit threshold for the clinical reading in response to the calculated current running average, wherein the current set upper limit threshold and/or the current set lower limit threshold varies over time;
    determining, over a predetermined monitoring time period, one or more breaches of at least one of a current set upper limit threshold and a current set lower limit threshold, wherein each breach is a breach event;
    calculating, over the predetermined monitoring time period, the total number of breach events for at least one of the upper limit threshold and the lower limit threshold;
    calculating a change in at least one of the upper and lower limit thresholds when the number of breaches of the upper and lower respective threshold exceeds a predetermined amount;
    generating a relative weight for at least one breach of the one or more breaches, wherein the relative weight of the at least one breach is a function of difference between a measurement of a magnitude of the at least one breach of the upper and the lower limit threshold and a current value of the running average; and
    generating an alarm in response to the number of breaches having a weighted value greater than a specified limit threshold value.

6. The method of claim 5, wherein a new upper limit threshold and a new lower limit threshold in subsequent defined time intervals are in response to a percentage of the running average, representative of a normal range of variability associated with measurements of a specific patient.

7. The method of claim 6, wherein the percentage is between 10% and 30% inclusive.

8. The method of claim 5 further comprising:
    identifying time points corresponding to the breaches of the upper and lower limit threshold; and
    determining a quantity of cumulative breaches based on a time frame.

* * * * *